United States Patent
Teshima et al.

(10) Patent No.: US 6,288,290 B1
(45) Date of Patent: Sep. 11, 2001

(54) METHOD FOR PRODUCTION OF HALOGEN-CONTAINING AROMATIC COMPOUND

(75) Inventors: Seiichi Teshima, West Lafayette, IN (US); Masayoshi Konishi; Kozo Tajiri, both of Tukuba (JP); Yoshinobu Asako, Amagasaki (JP); Sadao Miki, Kyoto (JP)

(73) Assignee: Nippon Shokubai, Co., Ltd., Osaka (JP)

( * ) Notice: Subject to any disclaimer, the term of this patent is extended or adjusted under 35 U.S.C. 154(b) by 0 days.

(21) Appl. No.: 09/420,860

(22) Filed: Oct. 19, 1999

(30) Foreign Application Priority Data

Oct. 20, 1998 (JP) .................................. 10-298664
Feb. 26, 1999 (JP) .................................. 11-050843
Feb. 26, 1999 (JP) .................................. 11-050844
Feb. 26, 1999 (JP) .................................. 11-050845

(51) Int. Cl.[7] .......................... C07C 19/08; C07C 22/00; C07C 47/52; C07C 47/57; C07C 17/00
(52) U.S. Cl. ....................... 570/129; 568/440; 204/157.99
(58) Field of Search ................ 204/157.99; 570/129; 568/440

(56) References Cited

U.S. PATENT DOCUMENTS 5,502,261    3/1996    Kleiner et al. .................... 570/196

FOREIGN PATENT DOCUMENTS

113185     *  7/1984  (EP) .
0 113 185 A1   7/1984  (EP) .
0 900 772 A1   3/1999  (EP) .
677199         8/1952  (GB) .

OTHER PUBLICATIONS

Dolbier et al., "A New and Practical Synthesis of Octafluoro [2,2]Paracyclophane", J. Org. Chem. 62:7500–7502, 1997. No Month Available.

(List continued on next page.)

Primary Examiner—Edna Wong
(74) Attorney, Agent, or Firm—Fish & Richardson P.C.

(57) ABSTRACT

This invention relates to a method for the production of an aromatic compound (II) having a $(CH_2)_nCX_2Br$ group (wherein X represents a fluorine or chlorine atom and the X's may be same or different, and n is an integer in the range of 0 to 4) by the reaction of photo-bromination of an aromatic compound (I) having a $(CH_2)_nCX_2H$ group (wherein X and n are as defined above) with a brominating agent, wherein the photo-bromination reaction is carried out while removing hydrogen bromide generated in the reaction system and/or in an atmosphere of a low oxygen content, and a halogen-containing naphthalene compound represented by the following formula (1):

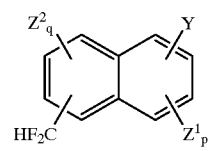

(1)

wherein Y represents $-CF_2H$, $-CF_2Br$, or $-CHO$ group, $Z^1$ and $Z^2$ independently represent a halogen atom, and p and q independently are an integer in the range of 0 to 3.

13 Claims, 10 Drawing Sheets

OTHER PUBLICATIONS

Dolbier et al., "A New Synthesis of Octafluoro[2,2]Paracyclophane", J. Org. Chem. 58:1827–1830, 1993. No Month Available.

Grechkina et al., "Synthesis of 1,1,2,2,9,9,10,10–Octafluoro [2,2]Para–Cyclophane", Zurnal Organicheskoi Khimmi 29(10):1999–2001, 1993 (with English Translation). No Month Available.

Fuqua et al., "Synthesis and Chemistry of Several Fluorinated p–Xylenes Designed as Precursors for . . . ", Tetrahedron 20:1625–1632, 1964. No Month Available.

He et al., "The Photochemical Synthesis of α,α,α–Bromodifluorotholuene and α,α,α–Chlorodifluorotoluene", Synthetic Communications 29:855–862, 1999. No Month Available.

Heble et al., "Mixed Laterally–Halogenated Toluenes", Journal of the Chemical Society 1322–1323, XP–002128333, 1938. No Month Available.

Haas et al., "Synthese Seitenkettenfluorierter Aromatischer Verbindungen und Deren Chemische Reaktivitat", Chem. Ber. 121:1329–1340, 1988. No Month Available.

* cited by examiner

Fig.3 Product 3

US 6,288,290 B1

METHOD FOR PRODUCTION OF HALOGEN-CONTAINING AROMATIC COMPOUND

BACKGROUND OF THE INVENTION

1. Field of the Invention

This invention relates to a method for the production of a halogen-containing aromatic compound useful as a raw material for resins which excel in heat resistance, chemical resistance and water repellency, and have a low dielectric and a low refractivity.

This invention further relates to a novel halogen-containing naphthalene compound useful as a raw material for resins which have a high glass transition temperature and excel in chemical resistance, water repellency, and low refractivity.

2. Description of the Related Art

It has been heretofore known that halogen-containing aromatic compounds, particularly those halogen-containing aromatic compounds which incorporate a difluoroalkyl group or a bromodifluoroalkyl group therein, are useful as raw materials for resins which excel in heat resistance, chemical resistance and water repellency, and have a low dielectric and a low refractivity. Among other halogen-containing aromatic compounds, particularly α,α'-dibromo-α,α,α',α'-tetrafluoro-p-xylene is known as constituting itself a raw material for per-α-fluoro[2,2]paracyclophane which is a precursor for poly(α,α,α',α'-tetrafluoro-p-xylene). For example, Journal of Organic Chemistry, Vol. 62, pp. 7500–7502, 1997 has stated that per-α-fluoro[2,2]paracyclophane derived from a halogen-containing aromatic compound can be used as a precursor for poly(α,α,α',α'-tetrafluoro-p-xylene) (referred to simply as "Parylene F" in the present specification) and that the Parylene F resulting from the polymerization thereof possesses a low dielectric constant and can be used an interlayer insulating film for semiconductors of the next generation. As means for the production of such a halogen-containing aromatic compound, a method which comprises irradiating an aromatic compound incorporating therein a $CX_2H$ group (wherein X represents F or Cl) with an UV light while using bromine ($Br_2$) as a brominating agent (Zhurnal Organicheskoi Khimii, 1993, 29, 1999) and a method which comprises effecting the irradiation with light while using N-bromosuccinimide as a brominating agent (Zhurnal Organicheskoi Khimii, 1993, 29, 1999; J. Org. Chem., 1993, 58, 1827–1830) have been known.

The former method which uses bromine ($Br_2$) as a brominating agent, however, has the problem of obtaining the target compound only in a low yield (27 to 30%). Then, the latter method which uses N-bromosuccinimide as a brominating agent, although indeed enables the relevant reaction to proceed efficiently, it still entails the problem of suffering succinimide to accumulate on the side of light incidence of the reaction vessel made of glass with the progress of the reaction and eventually impede the progress of this reaction and the problem of using N-bromosuccinimide, an expensive raw material, and consequently suffering the target product obtained by such a method to become inevitably expensive. Thus, none of the known methods is capable of producing a halogen-containing aromatic compound inexpensively in a high yield.

The semiconductor technology represents the existing forefront techniques for fine fabrication and mass production. The technology for the production of semiconductors culminates in the technique for fine fabrication and the technique for high density packaging. It has promoted the advance of semiconductors toward higher integration, greater addition to function, higher reliability, and lower cost. The formation in particular of a multilayer wiring which has emerged from the growth of high integration dictates fulfillment of such requirements as ample heat resistance, high electric insulation, low dielectric constant, high chemical and mechanical stability, and easy fine fabrication.

Since the Parylene F excels in insulation and yet possesses only such low thermal stability as 450° C., it fits only limited applications on account of insufficient heat resistance when higher heat resistance is required as, for example, in the process for the production of semiconductors. Various organic high polymers which are aimed at exalting ability of fabrication and facilitating impartation of varying properties have been developed and already adopted for actual use in numerous fields. It is, therefore, proper to conclude that the desirability of developing a resin excelling in heat resistance or a raw material for such a resin is rated very high.

SUMMARY OF THE INVENTION

An object of this invention, therefore, is to provide a method for producing a halogen-containing aromatic compound, particularly a halogen-containing aromatic compound incorporating a bromodifluoroalkyl group, inexpensively in a high yield.

Another object of this invention is to provide a halogen-containing naphthalene compound which is useful as a raw material for a resin which excels in heat resistance, chemical resistance and water repellency, have a low dielectric constant and a low refractivity.

The present inventors, while pursuing a study on the production of an aromatic compound (II) incorporating therein a $(CH_2)_nCX_2Br$ group by the reaction of photo-bromination of an aromatic compound (I) incorporating therein a $(CH_2)_nCX_2H$ group (wherein X represents a fluorine or chlorine atom and the X's may be same or different, and n is an integer in the range of 0 to 4) with a brominating agent, have found that the aromatic compound (II) aimed at can be obtained in a high yield by performing the reaction of photo-bromination by continuing removal of hydrogen bromide generated in the reaction system; and/or in an atmosphere of a low oxygen content by removing oxygen present in the reaction system prior to the reaction and/or continuing removal of oxygen during the course of the reaction; and optionally by combining the above step(s) suitably with a step of irradiating the reaction system with a light from a fluorescent lamp as a light source.

On the basis of the knowledge that the Parylene F can be produced by a process which comprises the steps of reduction, dimerization, cyclization, and etc. of 1,4-bis(bromodifluoro)benzene, the present inventors have selected various compounds in place of the 1,4-bis(bromodifluoro)benzene and measured glass transition temperatures of these compounds, to find that a halogen-containing naphthalene compound using a naphthalene ring in place of the benzene ring possesses characteristic properties ideal for this compound to be used as a raw material of a resin excelling in the property of glass transition temperature.

The present invention has been perfected based on this knowledge.

The objects mentioned above can be accomplished by a method for the production of an aromatic compound (II) having a $(CH_2)_nCX_2Br$ group (wherein X represents a fluorine or chlorine atom and the X's may be same or different, and n is an integer in the range of 0 to 4) by the reaction of photo-bromination of an aromatic compound (I) having a $(CH_2)_nCX_2H$ group (wherein x and n are as defined above) with a brominating agent, wherein the photo-bromination reaction is carried out while removing hydrogen bromide generated in the reaction system and/or in an atmosphere of a low oxygen content.

Further, the other object mentioned above can be accomplished by a halogen-containing naphthalene compound represented by the following formula (1):

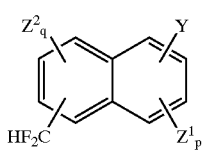

(1)

wherein Y represents —$CF_2H$, —$CF_2Br$, or —CHO group, $Z^1$ and $Z^2$ independently represent a halogen atom, and p and q independently are an integer in the range of 0 to 3.

The method of this invention permits a halogen-containing aromatic compound, particularly a halogen-containing aromatic compound incorporating therein a bromodifluoroalkyl group, which is useful as a raw material for a resin excelling in heat resistance, chemical resistance and water repellency, and having a low dielectric constant and a low refractivity to be produced inexpensively in a high yield. In the process for the production of the halogen-containing aromatic compound (II) by the reaction of photo-bromination, by performing the reaction of photo-bromination in particular i) by continuing removal of hydrogen bromide generated in the reaction system; and/or ii) in an atmosphere of a low oxygen content particularly by removing oxygen present in the reaction system prior to the reaction and/or continuing removal of oxygen during the course of the reaction; and optionally iii) by combining the above step(s) suitably with the step of irradiating the reaction system with a light from a fluorescent lamp as a light source, the aromatic compound (II) aimed at can be obtained in a high yield. Further, since the aromatic compound (II) can be obtained in a high yield, the purification of the product can be facilitated and the cost of production can be repressed.

According to this invention, a novel halogen-containing naphthalene compound can be provided. The halogen-containing naphthalene compound of this invention is useful as a raw material for a resin which excels in heat resistance, chemical resistance and water repellency, and has a low dielectric constant and a low refractivity.

The above and other objects, features, and advantages of the present invention will become clear from the following description of the preferred embodiments.

DESCRIPTION OF THE PREFERRED EMBODIMENTS

Figure 1:
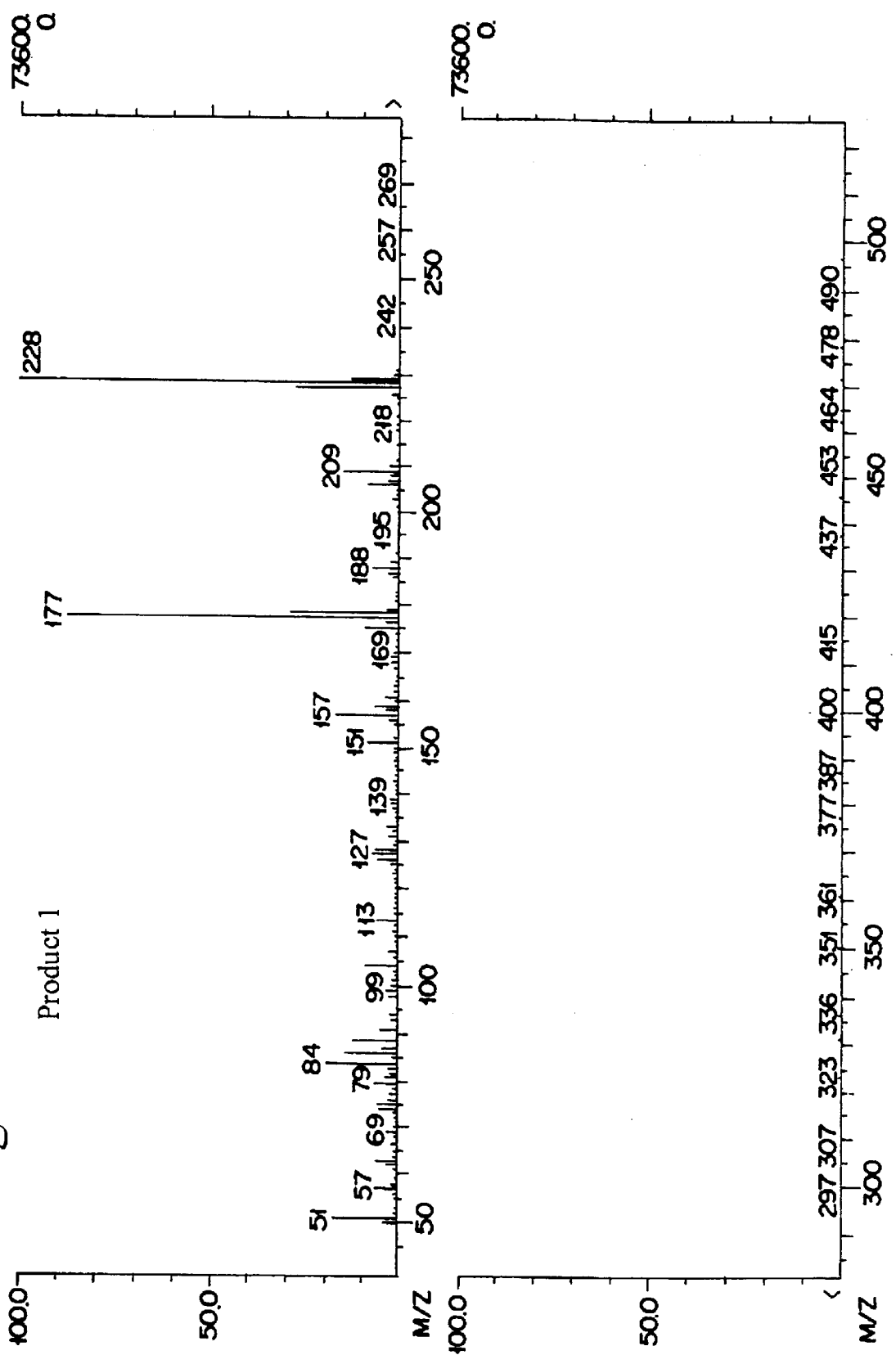
FIG. 1 is a GC-MS spectrum of 2,6-bis(difluoromethyl) naphthalene (Product 1).

This invention is to provide a method for the production of an aromatic compound (II) having a $(CH_2)_nCX_2Br$ group (wherein X represents a fluorine or chlorine atom and the X's may be same or different, and n is an integer in the range of 0 to 4) by the reaction of photo-bromination of an aromatic compound (I) having a $(CH_2)_nCX_2H$ group with a brominating agent, wherein the photo-bromination reaction is carried out while removing hydrogen bromide generated in the reaction system and/or in an atmosphere of a low oxygen content.

The aromatic compound (I) to be used as the raw material in the method of this invention is a compound which results from substituting the hydrogen atom in the aromatic ring thereof with the $(CH_2)_nCX_2H$ group. In the $(CH_2)_nCX_2H$ group mentioned above, each X represents a fluorine or chlorine atom, preferably a fluorine atom. The two X's may be identical or unidentical. Then, n is an integer in the range of 0 to 4, preferably 0 to 2, and more preferably 0.

The aromatic ring in the aromatic compound (I) to be used as the raw material in the method of this invention does not need to be particularly discriminated. As typical examples thereof, benzene, biphenyl, phenyl ether, indene, indane, naphthalene, 1,4-dihydronaphthalene, tetralin, biphenylene, acenaphtylene, acenaphtene, fluorene, phenanthrene, anthracene, fluoranthrene, aceanthrene, pyrene, 1-phenyl naphthalene, and 2-phenyl naphthalene may be cited. Among other aromatic rings cited above, benzene, naphthalene, and anthracene may be used advantageously, and benzene and naphthalene may be used particularly advantageously.

In this invention, the aromatic compound (I) essentially requires to have the $(CH_2)_nCX_2H$ group incorporated therein. The number of $(CH_2)_nCX_2H$ groups linked to the aromatic ring is not particularly limited but may be varied with the kind of the aromatic ring to be linked and the characteristic properties to be expected of the compound. For a benzene ring, for example, it may be generally in the range of 1 to 6, preferably 1 or 2. For a naphthalene ring, for example, it may be generally in the range of 1 to 8, preferably 1 or 2. For an anthracene ring, for example, it may be generally in the range of 1 to 10, preferably 1 or 2.

This invention allows the aromatic compound (I) to have incorporated therein a substituent other than the $(CH_2)_n CX_2H$ group. As typical examples of such other substituent, formyl group (—CHO), halogen atoms such as a chlorine atom (Cl), a bromine atom (Br), and fluorine atom (F), alkyl groups of 1 to 5 carbon atoms, preferably 1 to 3 carbon atoms, such as methyl, ethyl, propyl, isopropyl, butyl, isobutyl, and pentyl, the halogenated alkyl groups therefor such as bromodifluoromethyl, bromodichloromethyl, chlorodifluoromethyl, fluorodichloromethyl, trichloromethyl, and trifluoromethyl, alkoxy groups of 1 to 5 carbon atoms, preferably 1 to 3 carbon atoms such as methoxy, ethoxy, propoxy, isopropoxy, butoxy, isobutoxy, and pentoxy, and the halogenated alkoxy groups therefor such as bromodifluoromethoxy, bromodichloromethoxy, chlorodifluoromethoxy, fluorodichloromethoxy, trichloromethoxy, and trifluoromethoxy may be cited. Among other substituents cited above, formyl group, halogen atoms, particularly a fluorine atom, alkyl groups of 1 to 3 carbon atoms, i.e., methyl, ethyl, and isopropyl, the halogenated alkyl groups therefor, particularly bromodifluoromethyl (—CF$_2$Br) and bromodichloromethyl (—CCl$_2$Br) may be used advantageously as other substituents.

In this invention, the positions at which the (CH$_2$)$_n$CX$_2$H groups and other substituents are linked to the aromatic ring in the aromatic compound (I) are not particularly limited but may be varied with the kind of aromatic ring to be linked and the characteristic properties to be expected of the compound. With consideration to the reactivity of the polymerization to be subsequently performed and the properties of the polymer film to be formed, they may be preferably linked at symmetrical positions in the cyclic skeleton thereof.

As typical examples of the aromatic compound (I) which may be suitable as the raw material contemplated by this invention, therefore, α,α,α',α'-tetrafluoro-p-xylene, α,α,α',α'-tetrachloro-p-xylene, 2,6-bis(difluoromethyl)naphthalene, 2,6-bis(dichloromethyl)naphthalene, 2,6-bis(chlorofluoromethyl)naphthalene, 2-difluoromethyl-6-bromodifluoromethyl-naphthalene, 2-dichloromethyl-6-bromodifluoromethyl-naphthalene, 2-chlorofluoromethyl-6-bromodifluoromethyl-naphthalene, 2-difluoromethyl-6-bromodichloromethyl-naphthalene, 2-dichloromethyl-6-bromodichloromethyl-naphthalene, 2-chlorofluoromethyl-6-bromodichloromethyl-naphthalene, 6-difluoromethyl-2-formylnaphthalene, 6-dichloromethyl-2-formylnaphthalene, 6-chlorofluoromethyl-2-formylnaphthalene, 2,7-bis(difluoromethyl)naphthalene, 2,7-bis(dichloromethyl)naphthalene, 2,7-bis(chlorofluoromethyl)naphthalene, 2-difluoromethyl-7-bromodifluoromethyl-naphthalene, 2-dichloromethyl-7-bromodifluoromethyl-naphthalene, 2-chlorofluoromethyl-7-bromodifluoromethyl-naphthalene, 2-difluoromethyl-7-bromodichloromethyl-naphthalene, 2-dichloromethyl-7-bromodichloromethyl-naphthalene, 2-chlorofluoromethyl-7-bromodichloromethyl-naphthalene, 7-difluoromethyl-2-formylnaphthalene, 7-dichloro-methyl-2-formylnaphthalene, 7-chlorofluoromethyl-2-formylnaphthalene, 1,5-bis(difluoromethyl)naphthalene, 1,5-bis(dichloromethyl)naphthalene, 1,5-bis(chlorofluoromethyl)naphthalene, 1-difluoromethyl-5-bromodifluoromethyl-naphthalene, 1-dichloromethyl-5-bromodifluoromethyl-naphthalene, 1-chlorofluoromethyl-5-bromodifluoromethyl-naphthalene, 1-difluoromethyl-5-bromodichloromethyl-naphthalene, 1-dichloromethyl-5-bromodichloromethyl-naphthalene, 1-chlorofluoromethyl-5-bromodichloromethyl-naphthalene, 1-difluoromethyl-5-formylnaphthalene, 1-dichloromethyl-5-formylnaphthalene, 1-chlorofluoromethyl-5-formylnaphthalene, 1,4-bis(difluoromethyl)-2,3,5,6-tetrafluorobenzene, 1,4-bis(dichloromethyl)-2,3,5,6-tetrafluorobenzene, 1,4-bis(chlorofluoromethyl)-2,3,5,6-tetrafluorobenzene, 1,4-bis-(difluoromethyl)-2,3,5,6-tetrachlorobenzene, 1,4-bis(dichloromethyl)-2,3,5,6-tetrachlorobenzene, and 1,4-bis(chlorofluoromethyl)-2,3,5,6-tetrachlorobenzene; and compounds having a halogen atom, particularly a fluorine atom, substituted at a remaining position(s) may be cited. In this case, when the aromatic compound (I) happens to be a compound which has a hydrogen atom at an unsubstituted remaining position substituted with a halogen atom, the hydrogen atoms at all the remaining positions may be preferably substituted with halogen atoms, particularly fluorine atoms, in consideration of heat resistance, chemical resistance, water repellency, a low dielectric constant, and a low refractivity.

Among other compounds mentioned above, α,α,α',α'-tetrafluoro-p-xylene and halogen-containing naphthalene compounds represented by the following formula (1):

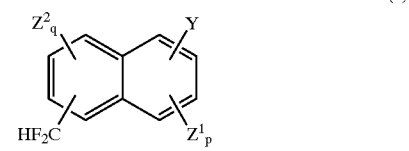

(1)

wherein Y represents —CF$_2$H, —CF$_2$Br, or —CHO group, $Z^1$ and $Z^2$ independently represent a halogen atom, and p and q independently are an integer in the range of 0 to 3, may be preferably used as the aromatic compound of the formula (I).

Particularly, the halogen-containing naphthalene compound represented by the formula (1) mentioned above is novel and excellent in heat resistance, chemical resistance and water repellency, and has a low dielectric constant and a low refractivity and, therefore, constitutes itself another aspect of this invention. That is, according to this other aspect of this invention, the present invention is to provide a halogen-containing naphthalene compound represented by the following formula (1):

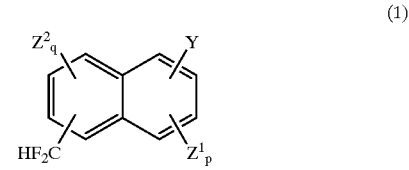

(1)

wherein Y represents —CF$_2$H, —CF$_2$Br, or —CHO group, $Z^1$ and $Z^2$ independently represent a halogen atom, and p and q independently are an integer in the range of 0 to 3. The formula (1) mentioned above means that the substituents, "Y", "—CF$_2$H", "$Z^1$", and "$Z^2$", can be linked at arbitrary positions in the naphthalene ring.

In the formula (1) mentioned above, Y represents —CF$_2$H, CF$_2$Br, or —CHO, preferably —CF$_2$H or —CHO, and more preferably —CF$_2$H; $Z^1$ and $Z^2$ independently represent a halogen atom such as a chlorine, bromine, or fluorine atom, preferably a chlorine or fluorine atom, and more preferably a fluorine atom; and p and q independently is an integer in the range of 0 to 3.

In the halogen-containing naphthalene compound represented by the formula (1) mentioned above, the positions to which the —CF$_2$H group and the substituent Y are linked are not particularly limited but may be preferably, in consideration of such factors as a glass transition temperature, symmetric positions, i.e., the 2 and 6 positions, in the cyclic skeleton thereof. The halogen-containing naphthalene compound of the formula (1) which particularly has difluoromethyl groups linked to both the 2 and 6 positions of the naphthalene ring may be advantageously used in this invention, because it can form a dimer as by heating, which dimer, when heated under a reduced pressure, can easily form a high polymer, and this high polymer thus obtained can possess a high glass transition temperature and excels in chemical resistance, water repellency, and low refractivity, and therefore, may be useful as a raw material for the production of a high polymer having such characteristic properties as heat resistance. The halogen-containing naphthalene compound of the formula (1) which incorporates a difluoromethyl group and a formyl group therein may be useful as an intermediate for pharmaceutical preparations and as an intermediate for liquid crystals and, therefore, can also be advantageously used in this invention.

The following six compounds, therefore, can be cited as typical examples of the halogen-containing naphthalene compound of the formula (1) which can be particularly advantageously used in this invention.

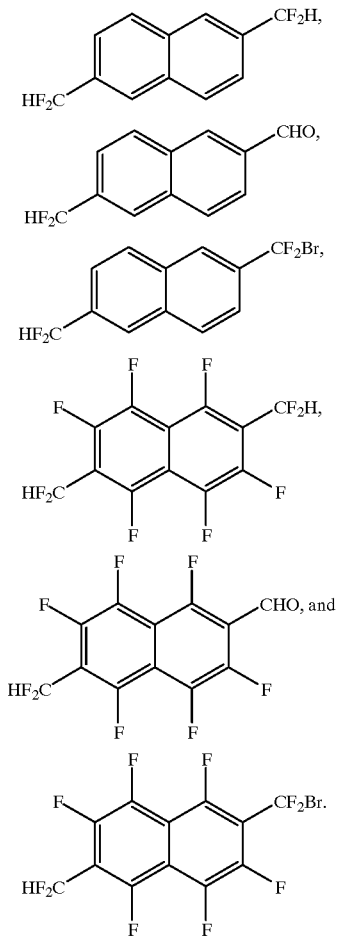

In this invention, the method to be used for producing the halogen-containing naphthalene compound represented by the formula (1) mentioned above does not need to be particularly limited but may be selected among conventional methods in the art. For example, a method which effects the production by using 2,6-naphthalene dicarbaldehyde (occasionally, hereinafter referred to simply as "NDA") as a raw material can be used. Incidentally, the NDA can be produced by the method which has been reported in Nippon Kagaku Kaishi, Vol. 3, pp. 603–605 (1974).

More specifically, the NDA can be synthesized as follows. Firstly, 2,6-naphthalene dicarboxylic acid is dispersed in phosphoryl chloride, adding dimethyl formamide (DMF) as kept stirred to the dispersion, refluxing the resultant mixture over a hot water bath, and distilling the produced reaction solution thereby expelling phosphoryl chloride by evaporation, to obtain 2,6-dichloroformyl naphthalene. The 2,6-dichloroformyl naphthalene and N-methyl aniline are refluxed in benzene over a hot water bath. The reaction product consequently formed is separated by filtration, washed with benzene, and dried to afford 2,6-naphthalene dicarbon-N-methyl anilide. The 2,6-naphthalene dicarbon-N-methyl anilide thus obtained is dispersed in THF. The dispersion and a solution of Li[AlH$_4$] in THF added dropwise thereto at 0° C. are left reacting at 0° C. for two hours. The reaction mixture consequently obtained is hydrolyzed in dilute hydrochloric acid. The resultant hydrolyzate is extracted from ether and distilled to expel the solvent by evaporation. The distillate is dissolved in acetone, mixed with water, and reprecipitated with an aqueous 20% acetone solution to obtain NDA.

Then, the NDA so synthesized is dissolved in dichloromethane and the produced solution as kept at a low temperature is acted on by diethylamino sulfur trifluoride under stream of an argon gas. As a result, 2,6-bis(difluoromethyl)naphthalene and 6-difluoromethyl-2-formylnaphthalene are synthesized in the resultant reaction solution simultaneously. These 2,6-bis(difluoromethyl)naphthalene and 6-difluoromethyl-2-formylnaphthalene can be separated as refined as by silica gel column chromatography, for example.

Further, the 2,6-bis(difluoromethyl)naphthalene thus obtained is dissolved in carbon tetrachloride, the produced solution is acted on by bromine under stream of an argon gas, and the resultant reaction solution is washed with sodium thiosulfate. As a result, 2,6-bis(bromodifluoromethyl)naphthalene and 2-bromodifluoromethyl-6-difluoromethylnaphthalene can be produced in the resultant reaction solution. These two compounds can be likewise separated as refined by a known method such as, for example, silica gel column chromatography.

Since the halogen-containing naphthalene compound of the formula (1) obtained as described above may be polymerized as by a heating or reducing treatment, it may be useful as a raw material for the production of a high polymer. Since the high polymer so obtained has a high glass transition temperature, the resin formed thereof can be applied as to the field of optical communication which demands heat resistance.

Here, the reaction of photo-bromination according to the method of this invention will be specified below.

In this invention, the reaction of photo-bromination does not need to be particularly discriminated but is only required to effect the reaction of an aromatic compound (I) with a brominating agent. Any of well-known methods which are available for the reaction of this kind under discussion may be adopted. The method of this invention, however, essentially comprises at least either feature of (a) a feature which comprises performing the reaction of photo-bromination meanwhile continuing removal of hydrogen bromide formed in the reaction system (first embodiment); or (b) a feature which comprises performing the reaction of photo-bromination in an atmosphere of a low oxygen content (second embodiment). Further, the method of this invention may preferably comprise (c) a feature which comprises performing the reaction of photo-bromination while irradiating the reaction system with a light from a fluorescent lamp as a light source (third embodiment) in combination with the above feature (a) and/or (b). As respects the form of combination of the above features, (a) to (c), though no particular discrimination is needed, the combinations of (a) and (b); (a) and (c); and (a), (b), and (c) prove to be advantageous.

In this invention, it is essential that the reaction of bromination be in the form of a photoreaction. If the reaction of bromination is not a photoreaction, the problem that the aromatic compound (II) is not obtained in a high yield would ensue. Further, the reaction of bromination ought to be a photoreaction in respect that the photoreaction improve the selectivity of reaction, obviate the necessity of heating at a high temperature, and therefore, promise a wide range of applications without reference to thermal stability of the product obtained by the reaction.

The constructions required commonly in the method contemplated by this invention will be described first and the constructions required differently in the first through third embodiment will be subsequently described herein below.

First, the common constructions for this invention will be described in detail below.

The brominating agent which can be used in this invention does not need to be particularly restricted but may be selected among agents heretofore known as available for the reaction. As typical examples thereof, bromine ($Br_2$), N-bromosuccinimide, and bromotrichloromethane may be cited. Among other brominating agents mentioned above, it is preferable to use a bromine-containing brominating agent, especially bromine itself as a brominating agent, in respect that bromine can be supplied at a low cost, i.e., the aromatic compound (II) aimed at can be produced inexpensively, and in consideration of such factors as the complexity, selectivity, and yield of the reaction. Particularly in the third embodiment which will be specifically described below, it is proper to use bromine, i.e., to be a bromine-containing brominating agent, especially bromine itself as the brominating agent, because the light-absorbing spectrum from the fluorescent lamp resembles the light-absorbing spectrum of bromine ($Br_2$) and therefore, the light emitted from the fluorescent lamp can be effectively used for the reaction of photo-bromination. In this invention, it should be noted that in the case of omitting the use of bromine, the reaction would be complicated and the selectivity and yield of the reaction would be lowered. Further, in this invention, if N-bromosuccinimide, for example, is used, it would possibly accumulate on the side of light incidence of the reaction vessel made of glass with the progress of the reaction and eventually interfere with the progress of the reaction (the incidence of light). Thus, when N-bromosuccinimide is used as the brominating agent, a photosensitizer capable of absorbing visible light may be additionally used.

Further, according to this invention, though the amount of the brominating agent to be used may be depend on the number of the $(CH_2)_n CX_2 H$ groups present in the aromatic compound (I) and does not need to be particularly limited, when the number of the $(CH_2)_n CX_2 H$ groups present in the aromatic compound (I) is Z, for example, the amount of the brominating agent to be used is generally in the range of 0.5×Z to 50×Z moles, desirably 1×Z to 20×Z moles, more desirably 1×Z to 10×Z moles, based on one mole of the aromatic compound (I). To be more specific, when the aromatic compound (I) having two $(CH_2)_n CX_2 H$ groups present therein is to be used, the amount of the brominating agent to be used is generally in the range of 1 to 100 moles, desirably 2 to 40 moles, more desirably 2 to 20 moles, based on one mole of the aromatic compound (I). If the amount of the brominating agent to be used is less than the lower limit of this range, the shortage would be at a disadvantage in unduly lowering the speed of the reaction of photo-bromination and seriously degrading the workability of bromination. Conversely, if this amount exceeds the upper limit of this range, the excess would be likewise at a disadvantage in being wasted without doing any good economically.

According to this invention, the brominating agent may be used in a form of mixture of two or more members. In this case, although the mixing ratio of each components of the brominating agent is not particularly limited, when the brominating agent contains bromine, for example, the mixing ratio of the bromine may be preferably in the range of 1 to 50% by weight, more preferably 10 to 40% by weight, based on the total amount of brominating agent to be used. If N-bromosuccinimide, for example, is used as a brominating agent other than bromine, it would possibly accumulate on the side of light incidence of the reaction vessel made of glass with the progress of the reaction and eventually interfere with the progress of the reaction (the incidence of light).

In this invention, the brominating agent may be collectively thrown into the reaction system prior to the reaction. Preferably, however, it may be gradually added to the reaction system in concert with the progress of the reaction of bromination by virtue of light.

The reaction vessel to be used in this invention does not need to be particularly discriminated but may be formed of any of the materials known to the art. Since it is fated to handle the reaction of photo-bromination, the reaction vessel is preferred to be capable of irradiating the reaction solution with light or capable of effecting the irradiation by means of a light source immersed in the reaction solution. As typical examples of the reaction vessel answering this description, a reaction vessel which is provided with a light source chamber made of clear Pyrex glass and isolated from the interior of the reaction vessel may be properly used. In this case, the light source chamber may be either directly contiguous or not contiguous with the reaction solution.

In this invention, the reaction of photo-bromination can be carried out without using a solvent. For the purpose of exalting the efficiency of removal of hydrogen bromides, however, it is commendable to use a solvent in the reaction. The solvent which can be used in this case does not need to be particularly limited but is only required to avoid substantially absorbing the light of a wavelength in the range of 390 to 600 nm, preferably 390 to 500 nm, and avoid being brominated. As typical examples of the solvent which fulfills the requirement, such halogen-containing solvents as dichloromethane, 1,2-dichloroethane, chloroform, 1,1,2,2-tetrachloroethane, carbon tetrachloride, and trichlorofluoromethane may be cited. Among other halogen-containing solvents cited above, carbon tetrachloride may be used preferably. The amount of the solvent to be used may be properly in the range of 1 to 100 parts by weight, preferably 5 to 30 parts by weight, based on 1 parts by weight of the aromatic compound (I).

The conditions for the reaction of photo-bromination according to this invention do not need to be particularly discriminated but are only required to enable the bromination of the aromatic compound (I) with a brominating agent to proceed efficiently. Properly, the reaction of photo-bromination may be carried out at a temperature of not less than 40° C., more preferably in the range of 45° to 200° C., and most preferably in the range of 70° to 150° C. If the reaction temperature is less than 40° C., the reaction would proceed very slowly and the production of the aromatic compound (II) in a high yield would possibly fail to occur. The reaction may be performed either under normal pressure, under pressure, or under a reduced pressure, whichever fits the occasion best. It is, however, preferred to be performed under normal pressure in consideration of such factors as the equipment. Further, the reaction period may be variable with the dosage of the light from the light source, the reaction temperature, and the concentrations of the aromatic compound (I) and brominating agent as the raw materials and is only required to attain the degree of conversion shown below.

Though the reaction of photo-bromination according to this invention may be terminated at any time selected arbitrarily, it is preferred to be terminated after the degree of conversion of the aromatic compound (II) aimed at has reached a level of not less than 90%.

Now, the first through third embodiments described above will be described respectively in detail below.

For a start, the first embodiment of this invention will be described below.

The reaction of photo-bromination according to the first embodiment must be carried out by continuously removing hydrogen bromide which is generated in the reaction system such as in the reaction molten solution or the reaction solution. If it is performed without continuously removing the hydrogen bromide, the problem that the aromatic compound (II) is not obtained in a high yield would ensue.

In the first embodiment, means for effecting the continuous removal of hydrogen bromide from the reaction system does not need to be particularly discriminated but may be selected among conventional methods. As typical examples of the method which answer this description, 1) a method which comprises blowing an inert gas such as nitrogen or argon into the reaction system and expelling the generated hydrogen bromide out of the system; 2) a method which comprises performing the reaction in a multiphase system with an organic phase/water phase and forcing the hydrogen bromide generated in the organic phase into the water phase; 3) a method which comprises allowing the presence of a solid base such as calcium carbonate or potassium carbonate in the reaction system and neutralizing the hydrogen bromide generated in the reaction systemwith the salt; and 4) a method which comprises allowing the presence of an oxidizing agent in the reaction system and using the oxidizing agent in converting the hydrogen bromide generated in the reaction system into bromine may be cited. Among other methods mentioned above, the methods 1) and 2) prove preferable because they are capable of obtaining the aromatic compound (II) aimed at with high selectivity. Optionally, these methods may be used as combined.

Of the methods for removing hydrogen bromide out of the reaction system, for the above 1), the velocity of blowing an inert gas into the reaction system is generally in the range of 1 to 100 ml/minute, preferably 5 to 50 ml/minute, per 100 ml of the solution. If the velocity of blowing an inert gas into the reaction system is less than 1 ml/minute, the removal of hydrogen bromide can not be satisfactorily attained. On the other hand, if it exceeds 100 ml/minute, the inert gas would have bromine and the reaction solvent incorporated therein, and be consumed wastefully. For the above 2), as typical examples of the organic solvent which can be used in the organic phase, dichloromethane, 1,2-dichloroethane, chloroform, 1,1,2,2-tetrachloroethane, and carbon tetrachloride may be cited. Alternatively, in the above 2), hydrogen bromide which is generated by the reaction may be forced into the water phase by using soley the water phase without the organic solvent. Among these processes, a process of using carbon tetrachloride as the organic solvent and a process of using no solvents may be preferably used. For the above 3), the amount of the solid base to be present is not generally particularly limited so as that it be not more than that capable of neutralizing the generated hydrogen bromide. For the above 4), as the oxidizing agent, conventional oxidizing agents may be similarly used and sodium periodate may be preferably used. In this case, the amount of the oxidizing agent used is not generally particularly limited so as that it be not more than that capable of oxidizing the generated hydrogen bromide into bromine.

In the first embodiment, as typical examples of the light source to be used for the reaction of photo-bromination, a fluorescent lamp, a high-pressure mercury-vapor lamp, and a tungsten halogen lamp may be cited. Among other light sources mentioned above, a fluorescent lamp is used particularly preferably as the light source because the spectrum of the light emitted from the fluorescent lamp resembles the light absorption spectrum of bromine ($Br_2$) and the light from the fluorescent lamp can be used effectively for the reaction of bromination. Properly, the fluorescent lamp as the light source may be coated with a well-known fluorescent material which emits a wavelength in the range of 390 to 600 nm, more preferably 390 to 500 nm. Properly, a color temperature of the fluorescent lamp may be generally not less than 5000 K and preferably fall within the range of 5000 to 10000 K.

The reaction of photo-bromination according to the first mode of embodiment, as described above, is preferred to be performed in an atmosphere of a low oxygen content. In this case, an oxygen content in the reaction system can be decreased by removing oxygen molecules present in the reaction system prior to the reaction and/or during the course of the reaction. If the removal of oxygen is not effected prior to the reaction nor during the course of the reaction, the reaction would be at a disadvantage in failing to obtain the aromatic compound (II) with high selectivity. Means adopted in this case for effecting the removal of oxygen from the reaction system does not need to be particularly discriminated but may be selected among methods heretofore known as available for the removal. As typical examples of the method answering the description, 1) a method which comprises blowing an inert gas such as nitrogen or argon into the reaction system and expelling the oxygen out of the system; and 2) a method which comprises placing the reaction system under a reduced pressure and expelling the oxygen by virtue of pressure difference may be cited.

Now, the second embodiment of this invention will be described herein below.

The reaction of photo-bromination according to the second embodiment must be performed after the oxygen content in the reaction system has been decreased by removing the oxygen present in the reaction system such as the reaction molten solution or the reaction solution prior to the reaction and/or while the oxygen content is continuously decreased by removing the oxygen generated in the reaction system during the course of the reaction, preferably after the oxygen content in the reaction system has been decreased by removing the oxygen prior to the reaction. If the removal of oxygen has not been effected prior to the reaction nor during the course of the reaction, the problem that the aromatic compound (II) can not be obtained with high selectivity would ensue.

In the second embodiment, the means for effecting the removal of oxygen from the reaction system does not need to be particularly discriminated but may be selected among the methods heretofore known as available for the removal. As typical examples of the method answering the description, 1) a method which comprises blowing an inert gas such as nitrogen or argon into the reaction system and expelling the oxygen out of the system; 2) a method which comprises placing the reaction system under a reduced pressure and expelling the oxygen by virtue of pressure difference; and 3) a method which comprises utilizing exposure to ultrasonic wave or vigorously agitating or the combination thereof may be cited. Optionally, these methods may be used as combined. In the case of the combination of these methods, the combinations of 1) and 2); 1) and 3); and 1), 2), and 3) prove to be advantageous.

Of the methods for removing oxygen out of the reaction system, for the above 1), the velocity of blowing an inert gas into the reaction system is generally in the range of 1 to 100 ml/minute, preferably 5 to 50 ml/minute, per 100 ml of the solution. If the velocity of blowing an inert gas into the reaction system is less than 1 ml/minute, the removal of oxygen can not be satisfactorily attained. On the other hand, if it exceeds 100 ml/minute, the inert gas would have bromine and the reaction solvent incorporated therein, and be consumed wastefully. In this case, the velocity of blowing an inert gas into the reaction system before and after the reaction may be the same or different. Further, the period of blowing an inert gas into the reaction system, when the reaction of photo-bromination is carried out while the oxygen is removed from the reaction system, is equal to the reaction time of photo-bromination. When the oxygen has been removed prior to the reaction, it is not particularly limited and only required to be capable of removing ample oxygen in the reaction system. The period of blowing an inert gas into the reaction system, however, is not less than 10 minutes, preferably not less than 30 minutes. For the above 2), the pressure in the reaction system is generally in the range of 10 to 100,000 Pa, preferably in the range of 100 to 50,000 Pa. For the above 3), a method for irradiating with ultrasonic wave is not particularly limited but may be such a method as being capable of removing ample oxygen in the reaction system. For example, a method for irradiating with ultrasonic wave in the range of 20 to 100 kHz, preferably in the range of 20 to 50 kHz for a period of not less than 10 minutes, preferably not less than 30 minutes can be adopted. Further, in the above 3), a stirring method is not particularly limited so as that it permit enough removal of oxygen in the reaction system. The stirring may be carried out at an agitation power of not less than $0.1$ $W/m^3$, preferably in the range of $0.1$ to $1000$ $W/m^3$ for a period of not less than 10 minutes, preferably not less than 30 minutes.

In the second embodiment, the light source to be used for the reaction of photo-bromination includes a fluorescent lamp, a high-pressure mercury-vapor lamp, and a tungsten halogen lamp. Among other light sources mentioned above, the fluorescent lamp is used particularly preferably as the light source because the spectrum of the light emitted from the fluorescent lamp resembles the light absorption spectrum of bromine ($Br_2$) and the light from the fluorescent lamp can be used effectively for the reaction of bromination. Properly, the fluorescent lamp as the light source may be coated with a known fluorescent material which emits a wavelength in the range of 390 to 600 nm, preferably 390 to 500 nm. Properly, the color temperature of the fluorescent lamp may be generally not less than 5000 K and preferably fall within the range of 5000 to 10000 K.

The reaction of photo-bromination according to the second embodiment, as described above, is preferred to be performed while the hydrogen bromide generated in the system is continuously removed from the system. If the reaction of photo-bromination is carried out without removing the hydrogen bromide generated in the system, the reaction would be at a disadvantage in failing to obtain the aromatic compound (II) aimed at in a high yield. The means for the removal of the hydrogen bromide from the reaction system in this case does not need to be particularly limited but may be selected among the methods heretofore known as available for the removal. The typical examples of the method answering this description may be identical with those already cited in the first embodiment.

The third embodiment of this invention will be described herein below.

The third embodiment requires the reaction of photo-bromination to use a fluorescent lamp as the light source. The reason for the use of a fluorescent lamp is that the spectrum of the light emitted from the fluorescent lamp resembles the light absorption spectrum of bromine ($Br_2$) and the light from the fluorescent lamp can be effectively used for the reaction of bromination. Properly, the fluorescent lamp to be used in this case as the light source may be coated with a well-known fluorescent material which emits a wavelength in the range of 390 to 600 nm, more preferably 390 to 500 nm.

The reaction of photo-bromination according to the third embodiment, as described above, is preferred to be performed during the continuous removal of the hydrogen bromide generated in the reaction system such as the reaction molten solution or the reaction solution. If the reaction is performed without removing the hydrogen bromide continuously, the problem that the aromatic compound (II) is not obtained in a high yield would ensue. The means for effecting the continuous removal of the hydrogen bromide from the reaction system does not need to be particularly discriminated but may be selected among the methods heretofore known as available for the removal. As typical examples of the method answering this description, those already cited in the first embodiment may be cited.

The reaction of photo-bromination according to the third embodiment may be preferably performed after the oxygen has been removed from the reaction system and/or while the removal of oxygen is continued during the course of the reaction. If the removal of oxygen is not effected prior to the reaction nor during the course of the reaction, the reaction would be at a disadvantage in failing to obtain the aromatic compound (II) with high selectivity. The means for effecting the removal of oxygen from the reaction system in this case does not need to be particularly limited but may be selected among the methods heretofore known as available for the removal. As typical examples of the method answering this description, those already mentioned in the second embodiment may be cited.

For the aromatic compound (II) to be produced by the method of this invention as described above, it is essential that the hydrogen atom at the terminal of the $(CH_2)_nCX_2H$ group in the aromatic compound (I) should be brominated, namely the aromatic compound (I) should be furnished with a $(CH_2)_nCX_2Br$ group (wherein X represents a fluorine or chlorine atom and the X's may be same or different, and n is an integer in the range of 0 to 4). When the aromatic compound (II) is furnished with at least two $(CH_2)_nCX_2Br$ groups, it proves particularly advantageous because it allows a wider range of applications as a raw material for a resin.

When the aromatic compound (II) to be produced by the method of this invention has two $(CH_2)_nCX_2Br$ groups, these $(CH_2)_nCX_2Br$ groups are preferably present at the most separated positions on the aromatic ring. When the aromatic ring happens to be a benzene ring, for example, the $(CH_2)_nCX_2Br$ groups are preferred to be substituted at mutually para positions. When the aromatic ring happens to be a naphthalene ring, properly the $(CH_2)_nCX_2Br$ groups are substituted at 2 and 6 positions, at 2 and 7 positions, or at 1 and 5 positions, most preferably at 2 and 6 positions.

Among other typical examples of the $(CH_2)_nCX_2Br$ groups, the $CF_2Br$ group proves particularly advantageous in terms of the width of the range of applications as a raw material for a resin of excellent heat resistance, a resin of a low water repellency, and a resin of a low dielectric constant.

As typical examples of the aromatic compound (II) to be advantageously produced by the method of this invention, α,α'-dibromo-α,α,α',α'-tetrafluoro-p-xylene, α,α'-dibromo-α,α,α',α'-tetrachloro-p-xylene, 2,6-bis(bromodifluoromethy)naphthalene, 2,6-bis(bromodichloromethyl)naphthalene, 2-bromodichloromethyl-6-bromodifluoromethyl-naphthalene, 6-bromodifluoromethyl-2-formylnaphthalene, 6-bromodichloromethyl-1-formylnaphthalene, 2,7-bis(bromodifluoromethyl)naphthalene, 2,7-bis(bromodichloromethyl)naphthalene, 2-bromodichloromethyl-7-bromodifluoromethyl-naphthalene, 7-bromodifluoromethyl-2-formylnaphthalene, 7-bromodichloromethyl-6-formylnaphthalene, 1,5-bis(bromodifluoro-methyl)naphthalene, 1,5-bis(bromodichloromethyl)naphthalene, 1-bromodichloromethyl-5-bromodifluoromethyl-naphthalene, 5-bromodifluoromethyl-1-formylnaphthalene, 5-bromodichloromethyl-1-formylnaphthalene, 1,4-bis(bromodifluoromethyl)-2,3,5,6-tetrafluorobenzene, 1,4-bis(bromodichloromethyl)-2,3,5,6-tetrafluorobenzene, 1,4-bis(bromodifluoromethyl)-2,3,5,6-tetrachlorobenzene, and 1,4-bis(bromodichloromethyl)-2,3,5,6-tetrachlorobenzene may be cited.

The aromatic compounds (II) contemplated by this invention have incorporated in the molecular units thereof such aromatic rings as benzene ring, naphthalene ring, and anthracene ring. The aromatic compounds (II) are preferred to have the $(CH_2)_n CX_2 Br$ groups directly substituted in the aromatic rings. Such an aromatic compound (II) may have the hydrogen in the aromatic ring substituted with a functional group other than the $(CH_2)_n CX_2 Br$ group. As typical examples of the functional group mentioned above, halogen groups such as a fluoro group, a bromo group, and a chloro group; alkyl groups such as a methyl group, an ethyl group, and a propyl group; perfluoroalkyl groups such as a trifluoromethyl group and a pentafluoroethyl group; and alkoxy groups such as a methoxy group, an ethoxy group, a perfluoromethoxy group, and a perfluoroethoxy group may be cited. These functional groups may be used either singly or in the form of a mixture of two or more members. Among other functional groups mentioned above, a fluoro group and a trifluoromethyl group prove particularly advantageous in terms of the width of range of applications as a raw material for a resin of excellent heat resistance, a resin of low water repellency, and a resin of a low dielectric constant.

After the reaction of bromination mentioned above has been completed, the aromatic compound (II) aimed at may be isolated and refined by known isolating and refining methods. As typical examples of the isolating and refining method which can be used, methods by distillation, column chromatography, recrystallization, and reprecipitation may be cited.

Now, this invention will be described more specifically below with reference to working examples of the invention. The time at which the reaction showed a sign of substantial stop of its advance was taken as the end point of the reaction. The yield of the reaction calculated at this end point was reported.

EXAMPLE 1

Synthesis of 2,6-naphthalene dicarbaldehyde 2,6-Naphthalene dicarbaldehyde is synthesized by following the procedure reported in the Journal of Japan Chemical Society, Vol.3, pp.603–605 (1974). This procedure is specifically described below.

First, 80 g of 2,6-naphthalene dicarboxylic acid is dispersed in 400 g of phosphoryl chloride. The dispersion kept thoroughly stirred and 8 g of dimethyl formamide (DMF) gradually added thereto are refluxed together on a hot water bath for 2.5 hours. After the ensuing reaction has been completed, the reaction mixture is distilled to expel phosphoryl chloride by evaporation. The residue of this distillation is recrystallized from benzene to obtain as needle crystals 61 g (yield: 65%) of 2,6-dichloroformylnaphthalene (melting point: 186° C.).

In 250 ml of benzene, 61 g (0.24 mol) of the 2,6-dichloroformylnaphthalene so obtained and 54 g (0.5 mol) of N-methyl aniline are refluxed over a hot water bath for 3.5 hours. The produced reaction mixture is cooled and separated by filtration, thoroughly washed with benzene, and dried. Then, the dried reaction mixture is recrystallized from dioxane to obtain 86 g (yield: 91%) of 2,6-naphthalene dicarbon-N-methyl anilide (melting point: 221°–223° C.).

In 30 ml of tetrahydrofuran (THF), 1.25 g of the 2,6-naphthalene dicarbon-N-methyl anilide so obtained is dispersed. To the resultant dispersion, a dispersion of 0.16 g of Li[AlH$_4$] in 30 ml of THF is added dropwise at 0° C. The resultant mixture is stirred for two hours with the reaction temperature kept at 0° C. Then, the produced reaction mixture is poured into dilute hydrochloric acid and left hydrolyzing therein. The hydrolyzate is left standing, extracted from ether, and distilled to expel the solvent by evaporation. The residue of distillation is dissolved in acetone and the produced solution, by addition of water till formation of an aqueous 20% acetone solution, is reprecipitated to obtain 0.31 g (yield: 50%) of 2,6-naphthalene discarbaldehyde (NDA) (melting point: 172.5°–173.5° C.).

EXAMPLE 2

Synthesis of 2,6-bis (difluoromethyl)naphthalene and 6-difluoromethyl-2-formylnaphthalene A three-neck glass flask having an inner volume of 1 liter was sealed, evacuated with a decompressing pump to 10 mmHg, and then filled with argon gas (water content of 18 volppm) till normal pressure (atmospheric pressure). Subsequently, the three-neck flask was fitted with a stirrer as kept swept with argon gas and charged with 7.52 g (40.9 m.mols) of the NDA synthesized in Example 1 and 500 ml of dehydrated dichloromethane and the contents of the flask were stirred till thorough solution was obtained.

The three-neck flask now filled with the resultant solution was immersed in ice water at 3.0° C. To the solution kept at this temperature, 17 ml (129 m.mols) of diethylaminosulfuric acid trifluoride (DAST) was slowly added. Subsequently, the contents of the flask were continuously stirred at 23° C. for 12 hours, with the interior of the flask kept swept with argon gas. When the produced reaction solution was slowly transferred into ice water and extracted from dichloromethane, a Reaction Solution A was consequently obtained.

When the reaction solution was analyzed by gas chromatography mass spectrometry (GC-MS), the formation therein of 6-difluoromethyl-2-formylnaphthalene (Product 2) and 2,6-bis(difluoromethyl)naphthalene (Product 1) was confirmed.

The Reaction Solution A mentioned above, when isolated and refined by means of column chromatography with silica gel, produced 5.9 g (yield: 63%) of 2,6-bis (difluoromethyl) naphthalene.

Figure 2:
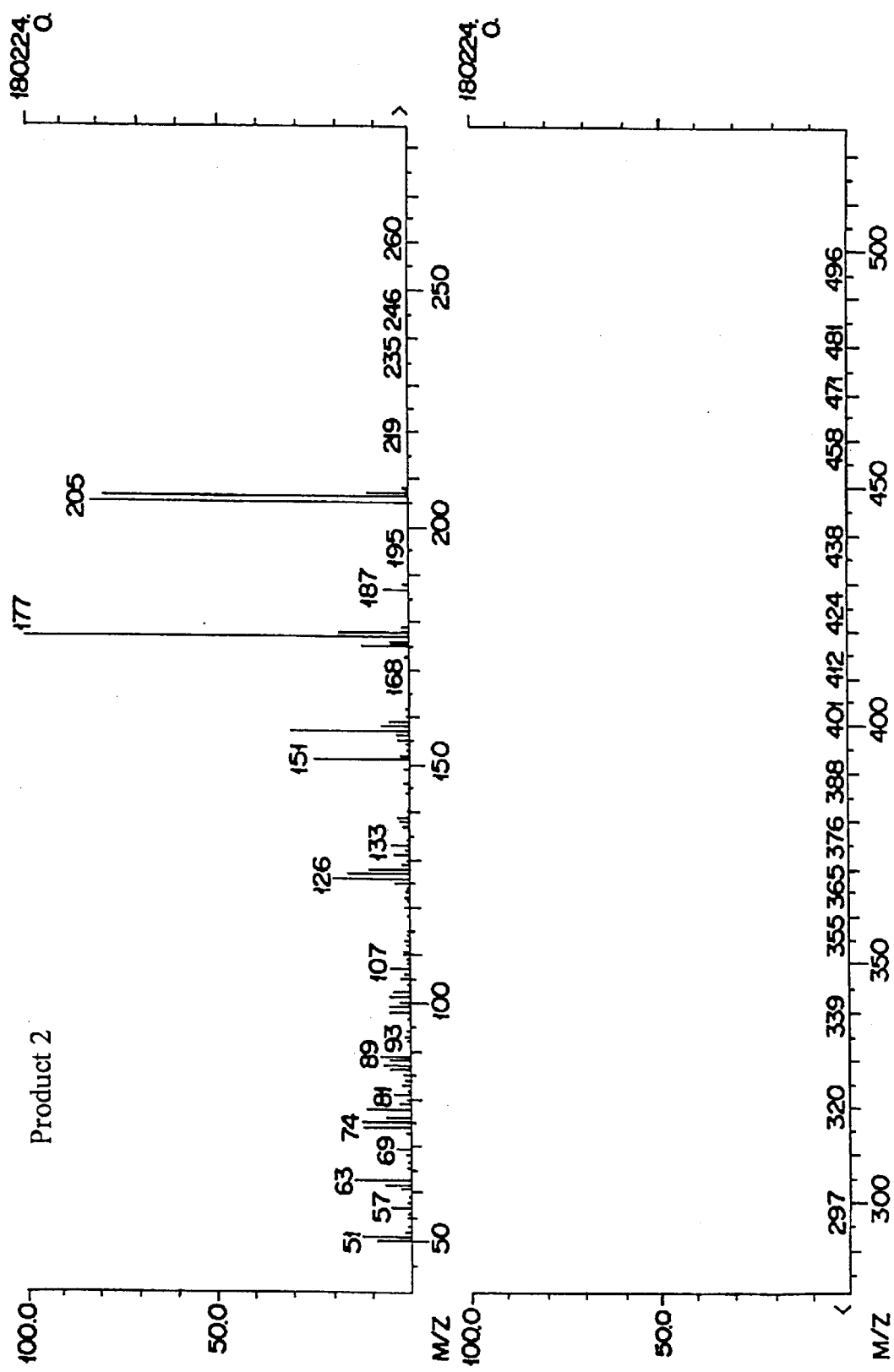
FIG. 2 is a GC-MS spectrum of 6-difluoromethyl-2-formyl naphthalene (Product 2).

The results of the analysis of Product 1 and Product 2 are shown below. The GC-MS spectra of these Products 1 and 2 are shown respectively in FIG. 1 and FIG. 2 and the $^1$H-NMR, $^{13}$C-NMR, and $^{19}$F-NMR charts of the Product 1 are shown in FIGS. 5 to 10.

(1) 2,6-Bis(difluoromethyl)naphthalene (Product 1):
  (a) Mass spectrum 228 (M$^+$)
  (b) $^1$H-NMR;
    Chemical shift, . (ppm): (Solvent; CDCl$_3$, internal standard substance; TMS)
  (c) $^{13}$C-NMR;
    Chemical shift, . (ppm): (Solvent; CDCl$_3$, internal standard substance; TMS)
  (d) $^{19}$F-NMR;
    Chemical shift, . (ppm): (Solvent; CDCl$_3$, internal standard substance; trifluoroacetic acid)

(2) 6-Difluoromethyl-1-formylnaphthalene (Product 2)
  (a) Mass spectrum 206 (M$^+$)

EXAMPLE 3

Synthesis of 2,6-bis (bromodifluoromethyl)naphthalene and 2-bromodifluoromethyl-6-difluoromethylnaphthalene In a separable flask having an inner volume of 100 ml and provided with a condenser, a gas inlet tube, and a ribbon heater, 0.21 g (0.9 m.mol) of the 2,6-bis(difluoromethyl)naphthalene synthesized in Example 2 and 20 ml of carbon tetrachloride were placed and stirred till thorough solution was obtained. The produced solution was bubbled with argon gas for 30 minutes, added with 0.5 ml (9.7 m.mol) of bromine, and heated to 80° C.

Subsequently, the produced solution in the separable flask was bubbled with argon gas and irradiated with a light from a 25 W fluorescent lamp through the bottom side of the flask for 120 hours.

After the reaction, the solution was washed with an aqueous sodium thiosulfate solution and then analyzed by GC-MS. As a result of this analysis, the formation of 2,6-bis(bromodifluoromethyl)naphthalene (Product 3) and 2-bromodifluoromethyl-6-difluoromethylnaphthalene (Product 4) was confirmed.

The reaction solution mentioned above, when isolated and refined by column chromatography with silica gel, produced 0.17 g (yield: 50%) of 2,6-bis(bromodifluoromethyl)naphthalene.

Figure 3:
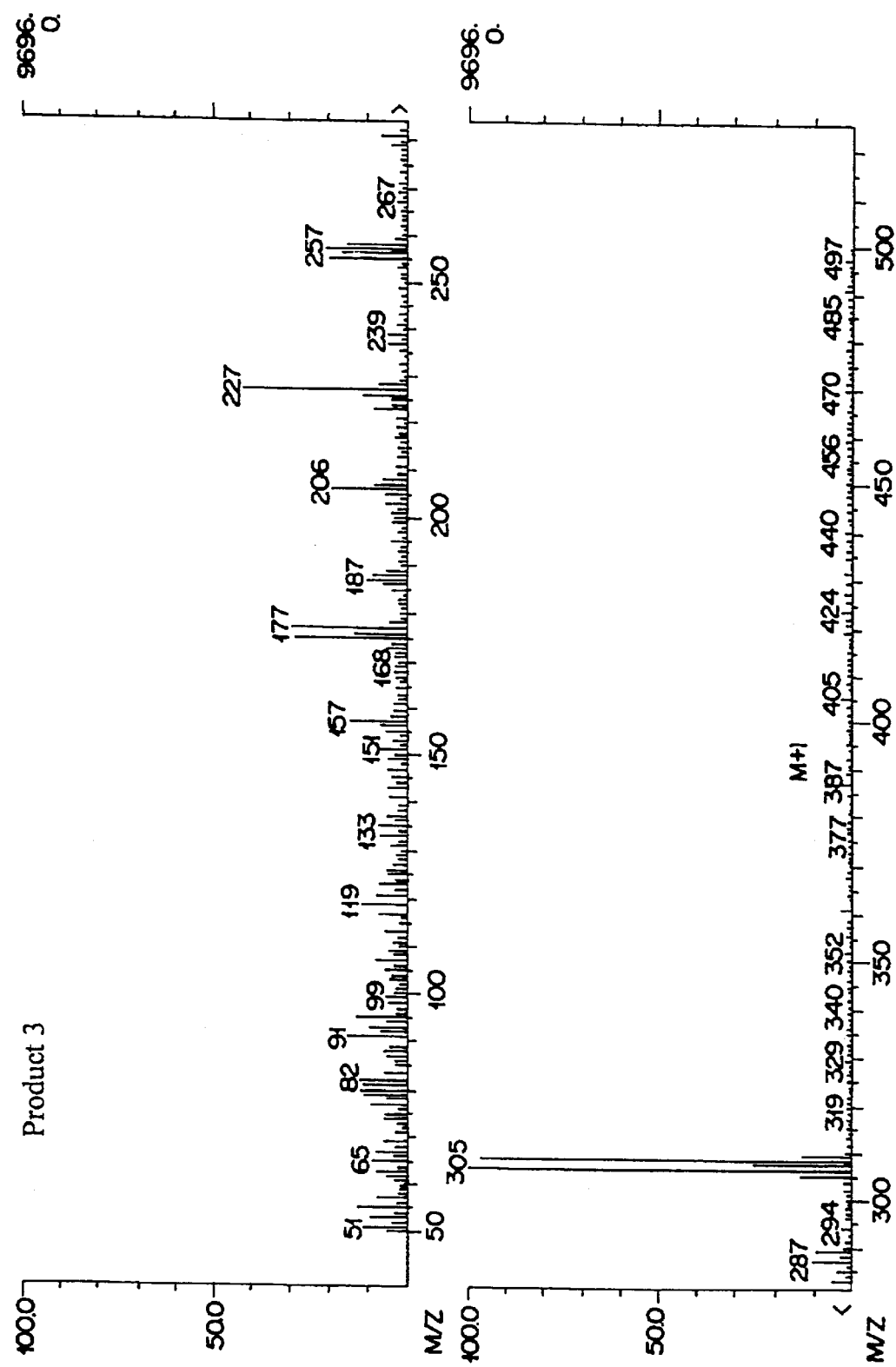
FIG. 3 is a GC-MS spectrum of 2,6-bis (bromodifluoromethyl)naphthalene (Product 3).
Figure 4:
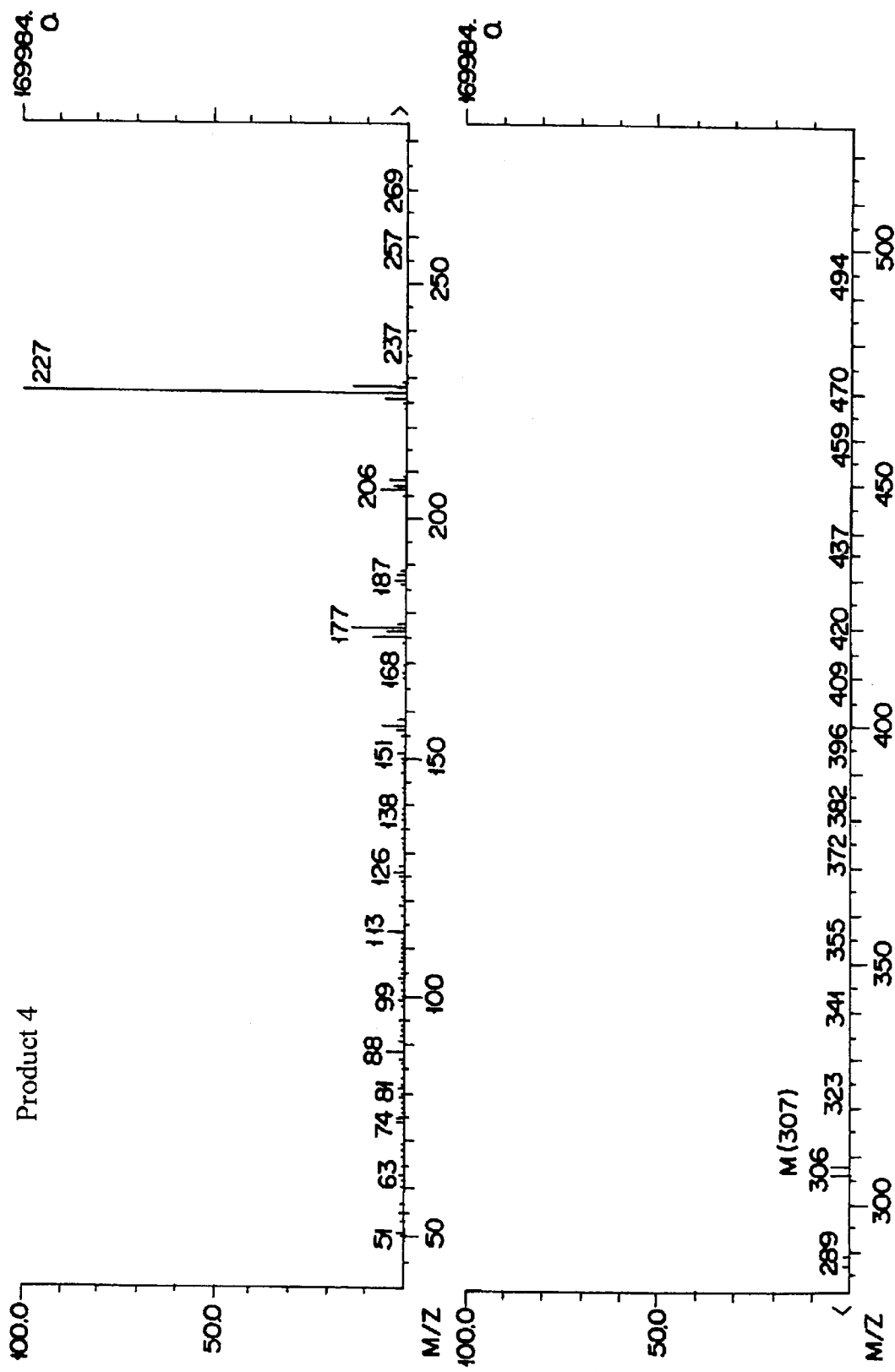
FIG. 4 is a GC-MS spectrum of 2-bromodifluoromethyl-6-difluoromethyl naphthalene (Product 4).
Figure 5:
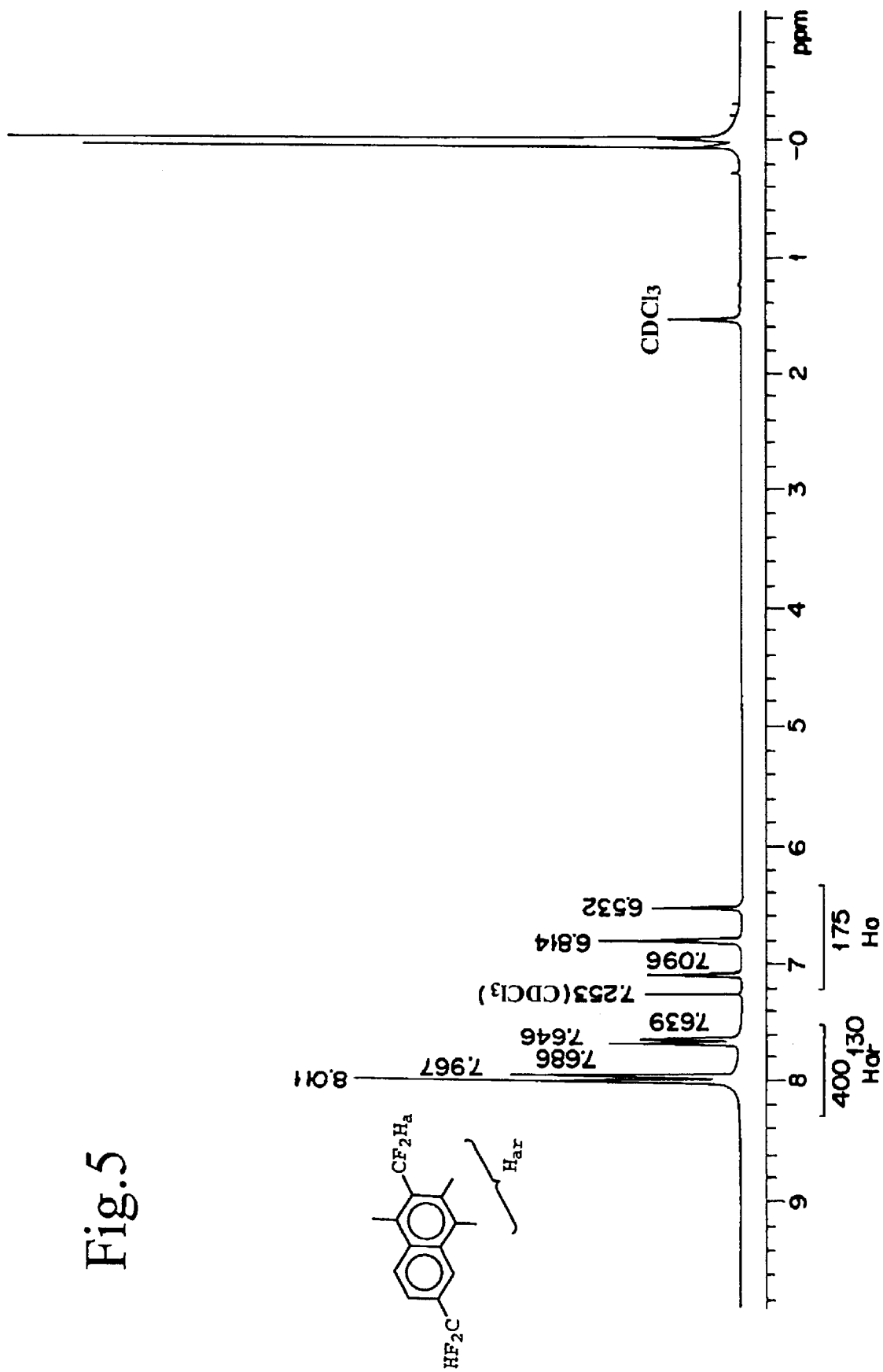
FIG. 5 is a $^1$H-NMR chart of 2,6-bis(difluoromethyl) naphthalene (Product 1).
Figure 6:
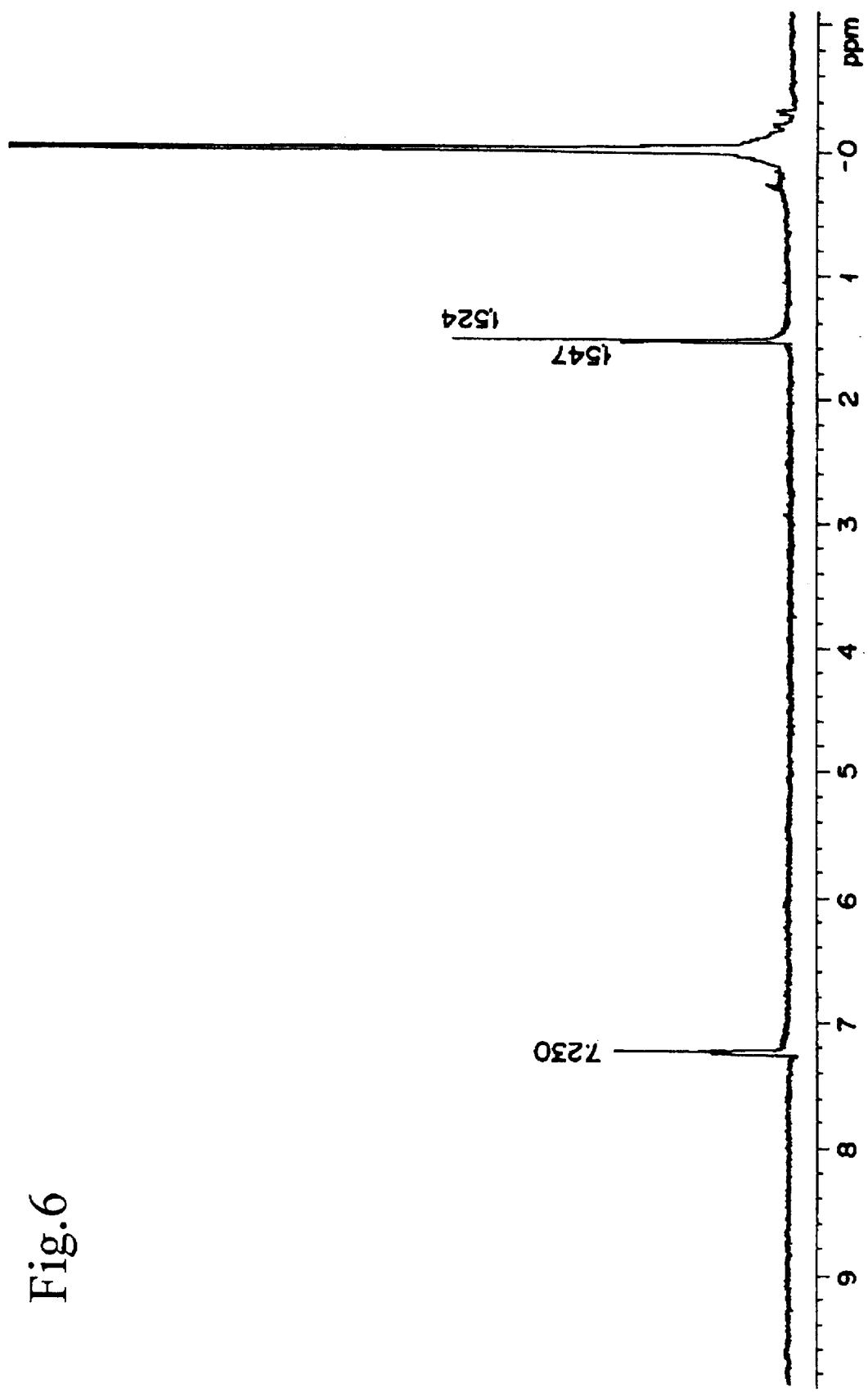
FIG. 6 is a $^1$H-NMR chart solely of the solvent.
Figure 7:
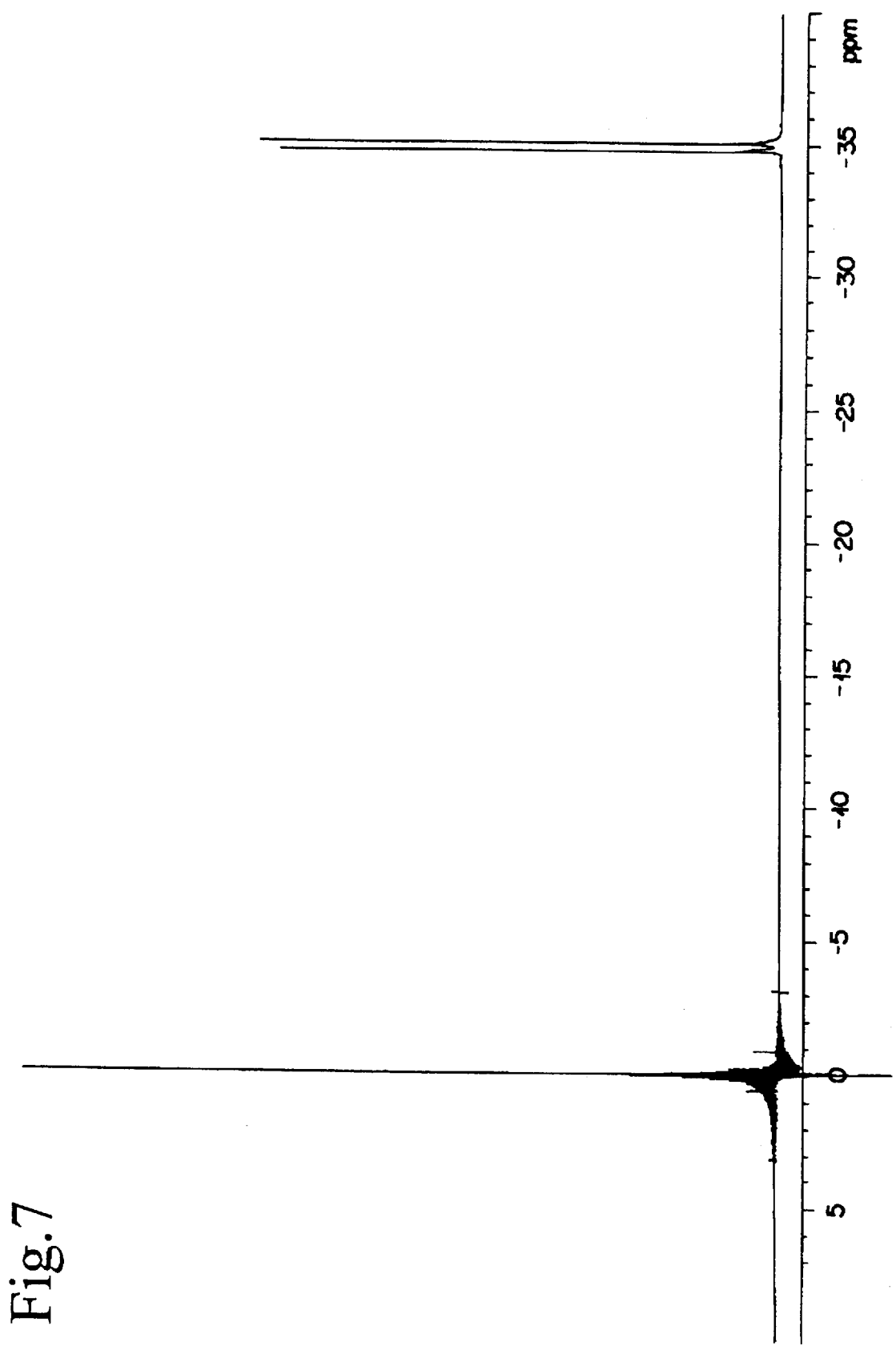
FIG. 7 is a $^{19}$F-NMR chart of 2,6-bis(difluoromethyl) naphthalene (Product 1).
Figure 8:
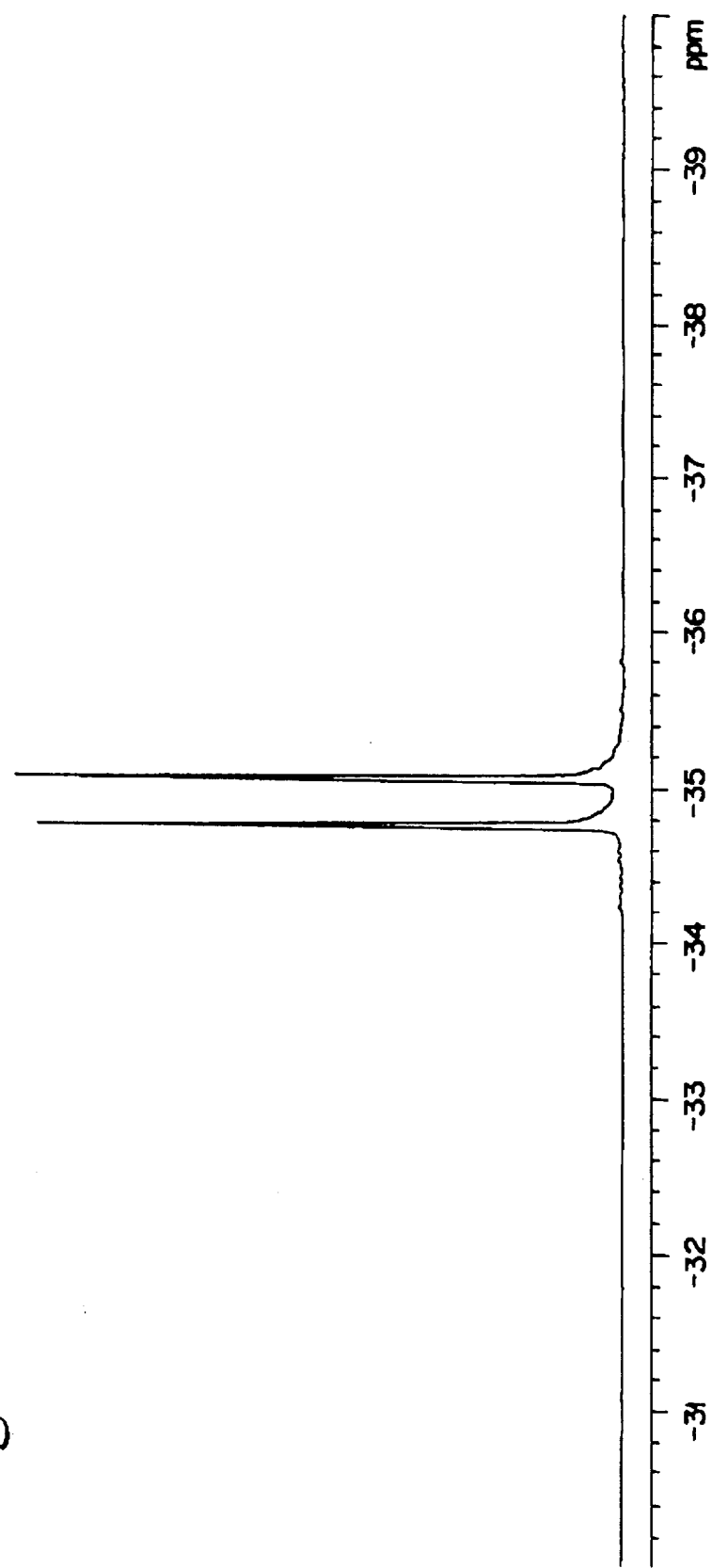
FIG. 8 is a $^{19}$F-NMR chart of 2,6-bis(difluoromethyl) naphthalene (Product 1).
Figure 9:
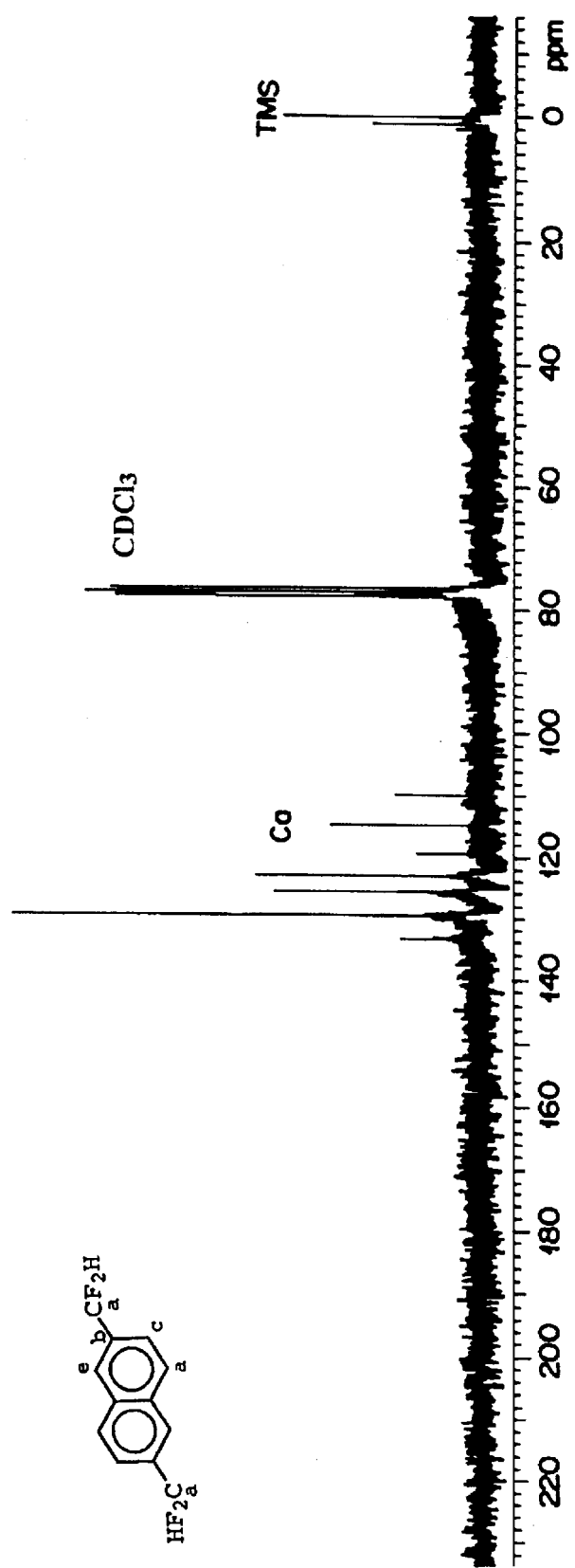
FIG. 9 is a $^{13}$C-NMR chart of 2,6-bis(difluoromethyl) naphthalene (Product 1).
Figure 10:
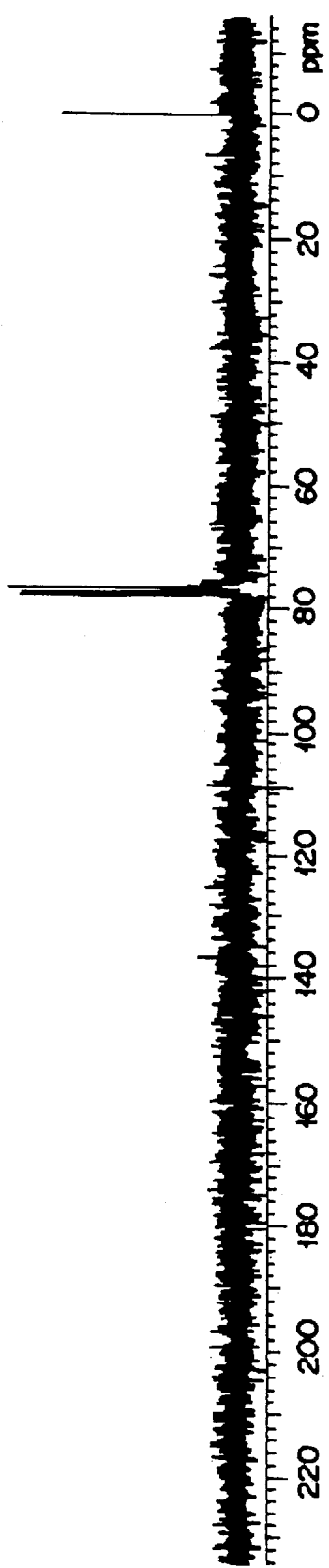
FIG. 10 is a $^{13}$C-NMR chart of the solvent.

The results of the analysis of Products 3 and 4 are shown below. The GC-MS spectra of Products 3 and 4 are respectively shown in FIG. 3 and FIG. 4.
(3) 2,6-Bis(bromodifluoromethyl)naphthalene (Product 3):
  (a) Mass spectrum 387 (M$^+$)
(4) 2-Bromodifluoromethyl-6-difluoromethylnaphthalene (Product 4):
  (a) Mass spectrum 307 (M$^+$)

EXAMPLE 4

Effect of Removal of Hydrogen Bromide

In a reaction device made of Pyrex glass and provided with an argon gas inlet tube, 60 ml of carbon tetrachloride and 8.9 g (0.05 mol) of 1,4-bis(difluoromethyl)benzene were placed and bubbled with argon gas (flow rate 10 ml/min) for 30 minutes. The produced mixture in the device was heated till reflux of the carbon tetrachloride, added with 5.1 ml (0.1 mol) of bromine, and irradiated with the light from a tungsten halogen lamp (500 W) set in place inside a reaction vessel. The reaction temperature was 80° C. The reaction was performed, with the reaction solution bubbled continuously with argon gas and the generated hydrogen bromide removed therefrom. The removal of the hydrogen bromide was confirmed by the change of the pH value of 50 ml of the trapped water to the acid side (not more than pH 2) after the reaction. During the course of this reaction, bromine was added in a fixed volume of 2 ml (0.039 mol) to the solution at intervals of 6 hours.

The resultant reaction solution was irradiated with the light from a tungsten halogen lamp (500 W) for 6 hours and then analyzed by GC-MS to confirm the formation of 1,4-bis(bromodifluoromethyl)benzene (Product 5) and 1-bromodifluoromethyl-4-difluoromethylbenzene (Product 6). By the GC analysis performed separately, the relative ratio of the raw material, Product 5, and Product 6 was found to be 70/25/5.

The reaction solution obtained similarly after 48 hours+ irradiation with the light from a tungsten halogen lamp (500 W), when concentrated, refined, and separated, afforded 14.3 g (yield: 85%) of Product 5.
Control 1: System Saturated with Hydrogen Bromide Photo-bromination was performed by following the procedure of Example 4 except that an UV lamp was used in place of the tungsten halogen lamp (500 W) as the light source and the bubbling with argon gas was omitted.

When the reaction solution consequently obtained was subjected to the GC-MS analysis and the GC analysis in the same manner as in Example 4, the yield of Product 5 was found to be 25%.
Control 2

Photo-bromination was performed by following the procedure of Control 1 while the light source was changed from the UV lamp to a fluorescent lamp. The yield of Product 5 was found to be 30%.

EXAMPLE 5

Removal of Hydrogen Bromide by Hydration

Photo-bromination was performed by following the procedure of Example 4 while further adding 5 ml of water to the reaction system and irradiating the system with the light from a tungsten halogen lamp (500 W) instead of bubbling the solution with argon gas. When the water phase was tested for pH after 48 hours' irradiation, the pH value was found to be changed toward the acid side (pH 3) as compared with that which existed prior to the reaction.

When the reaction solution thus obtained was concentrated, refined, and separated in the same manner as in Example 4, it produced 14.0 g (yield: 83%) of Product 5.
Control 3: Removal of Hydrogen Bromide by System Saturated with Hydrogen Bromide Photo-bromination was performed by following the procedure of Example 4 while further adding 5 g of water saturated with hydrogen bromide to the reaction system and irradiating the system with the light from a fluorescent lamp instead of bubbling the system with argon gas. After the irradiation was continued for 48 hours, the solution showed no discernible sign of the formation of Product 5 or Product 6.

EXAMPLE 6

Removal of Hydrogen Bromide with NaIO$_4$

Photo-bromination was performed by following the procedure of Example 4 while adding 5 ml of an aqueous 10% sodium periodate ($NaIO_4$) solution instead of bubbling the solution with argon gas. When the reaction solution resulting from 48 hours' irradiation with the light was concentrated, refined, and separated in the same manner as in Example 4, it produced 13.5 g (yield: 80%) of Product 5.

EXAMPLE 7

Removal of Oxygen

In a reaction device made of Pyrex glass and provided with a condenser and an argon gas inlet tube, 60 ml of carbon tetrachloride and 8.9 g (0.05 mol) of 1,4-bis (difluoromethyl)benzene were placed and bubbled with argon gas (flow rate 10 ml/min) as vigorously stirred for 30 minutes so as to deprive the solution of oxygen. The produced mixture in the device was heated till reflux of the carbon tetrachloride, added with 5.1 ml (0.1 mol) of bromine, and irradiated with the light from a tungsten halogen lamp (500 W) set in place inside a reaction vessel. The reaction temperature was 80° C. The reaction was performed, with the reaction solution bubbled continuously with argon gas and the generated hydrogen bromide removed therefrom. The removal of the hydrogen bromide was confirmed by the change of the pH value of 50 ml of the trap water to the acid side (not more than pH 2) after the reaction. During the course of this reaction, bromine was added in a fixed volume of 2 ml (0.039 mol) to the solution at intervals of 6 hours.

The resultant reaction solution was irradiated with the light from a tungsten halogen lamp (500 W) for 6 hours and then analyzed by GC-MS to confirm the formation of 1,4-bis(bromodifluoromethyl)benzene (Product 5) and 1-bromodifluoromethyl-4-difluoromethylbenzene (Product 6). By the GC analysis performed separately, the relative ratio of the raw material, Product 5, and Product 6 was found to be 70/25/5.

The reaction solution obtained similarly after 48 hours' irradiation with the light from a tungsten halogen lamp (500 W), when concentrated, refined, and separated, afforded 14.3 g (yield: 85%) of Product 5.

Control 4: Omission of Ar Bubbling (Influence of $O_2$)

In a reaction device made of Pyrex glass and provided with a condenser (which equaled to the reaction device used in Example 7 excepting for the omission of the argon gas inlet tube), 60 ml of carbon tetrachloride and 8.9 g of 1,4-bis(difluoromethyl)benzene were placed. The mixture consequently formed was heated till reflux of the carbon tetrachloride and made to add 5.1 ml (0.1 mol) of bromine. Then, the mixture was irradiated with the light from a tungsten halogen lamp (500 W) set in place in the reaction solution. The white precipitate formed in the mixture after 48 hours' irradiation with the light was separated by filtration. When the filtrate was analyzed by GC-MS, the formation of 1,4-bis(bromodifluoromethyl)benzene (Product 5) and 1-bromodifluoromethyl-4-difluoromethylbenzene (product 6) was confirmed.

When the reaction solution resulting from 48 hours' irradiation with the light was concentrated, refined, and separated, it produced 5.1 g (yield: 30%) of Product 5.

When the white precipitate mentioned above was separately analyzed by IR, the absorption originating in a carboxyl group was confirmed. From the results, it is inferred that the reaction of the intermediate of reaction with oxygen by-produced carboxylic acid.

Control 5: System Saturated with Hydrogen Bromide

Photo-bromination was performed by following the procedure of Example 7 except that an UV lamp was used in place of the tungsten halogen lamp (500 W) as the light source and the bubbling with argon gas was omitted.

When the reaction solution consequently obtained was subjected to the GC-MS analysis and the GC analysis in the same manner as in Example 7, the yield of Product 1 was found to be 25%.

Control 6

Photo-bromination was performed by following the procedure of Control 5 while the light source was changed from the UV lamp to a fluorescent lamp. The yield of Product 5 was 30%.

EXAMPLE 8

Effect of Fluorescent Lamp

In a reaction device made of Pyrex glass and provided with a condenser and an argon gas inlet tube, 60 ml of carbon tetrachloride and 8.9 g (0.05 mol) of 1,4-bis (difluoromethyl)benzene were placed and bubbled with argon gas (flow rate 10 ml/min) for 30 minutes. The produced mixture in the device was heated till reflux of the carbon tetrachloride, added with 5.1 ml (0.1 mol) of bromine, and irradiated with the light from a fluorescent lamp (7.5 W) set in place inside a reaction vessel. The reaction temperature was 80° C. The reaction was performed, with the reaction solution bubbled continuously with argon gas and the generated hydrogen bromide removed therefrom. The removal of the hydrogen bromide was confirmed by the change of the pH value of 500 ml of the trap water to the acid side (not more than pH 2) after the reaction. During the course of this reaction, bromine was added in a fixed volume of 2 ml (0.039 mol) to the solution at intervals of 6 hours.

The resultant reaction solution was irradiated with the light for 6 hours and then analyzed by GC-MS to confirm the formation of 1,4-bis(bromodifluoromethyl)benzene (Product 5) and 1-bromodifluoromethyl-4-difluoromethylbenzene (Product 6). By the GC analysis performed separately, the relative ratio of the raw material, Product 5, and Product 6 was found to be 50/40/10.

The reaction solution obtained similarly after 48 hours' irradiation with the light, when concentrated, refined, and separated, afforded 14.0 g (yield: 83%) of Product 5.

EXAMPLE 9

Photo-bromination was performed by following the procedure of Example 8 except that a tungsten halogen lamp (500 W) was used in place of the fluorescent lamp (7.5 W) as the light source. The reaction solution obtained similarly after 48 hours' irradiation with the light, when concentrated, refined, and separated, afforded 14.3 g (yield: 85%) of Product 5.

Control 7

Photo-bromination was performed by following the procedure of Example 8 except that an UV lamp was used in place of the fluorescent lamp (7.5 W) as the light source and the bubbling with argon gas was omitted.

When the reaction solution consequently obtained was subjected to the GC-MS analysis and the GC analysis in the same manner as in Example 8, the yield of Product 5 was found to be 25%.

The entire disclosure of Japanese Patent Application Nos. 10-298664, 11-50843, 11-50844, and 11-50845 filed on Oct. 20, 1998, Feb. 26, 1999, Feb. 26, 1999, and Feb. 26, 1999 including specification, claims, drawings and summary are incorporated herein by reference in its entirety.

What is claimed is:

1. A method for the production of an aromatic compound (II) having a $(CH_2)_nCX_2Br$ group, wherein X represents a fluorine or chlorine atom and the X's may be the same or different, and n is an integer in the range of 0 to 4, by said method comprising the step of reacting an aromatic compound (I) having a $(CH_2)_nCX_2H$ group, wherein X and n are as defined above, with a brominating reagent, in a photo-bromination reaction, wherein the photo-bromination reaction is carried out in an atmosphere of a low oxygen content.

2. A method according to claim 1, wherein said brominating reagent is bromine.

3. A method according to claim 1, wherein said reaction of photo-bromination is performed after the oxygen present in the reaction system has been removed prior to the reaction and/or while the removal of the oxygen is continued during the course of the reaction.

4. A method according to claim 1, wherein said reaction of photo-bromination is performed while the reaction system is continuously irradiated with a light from a fluorescent lamp as a light source.

5. A method according to claim 4, wherein said photo-bromination reaction is carried out while removing hydrogen bromide generated in the reaction system.

6. A method according to claim 1, wherein the temperature during the reaction of photo-bromination is not less than 40° C.

7. A method according to claim 1, wherein said reaction of photo-bromination is performed with continuous irradiation of the reaction system with a light having a wavelength in the range of 390 to 600 nm.

8. A method according to claim 1, wherein said aromatic compound (I) is α,α,α',α'-tetrafluoro-p-xylene or a compound represented by the following formula (1):

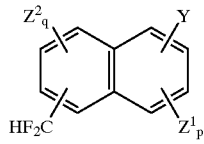
(1)

wherein Y represents —$CF_2H$, —$CF_2Br$, or —CHO group; $Z^1$ and $Z^2$ independently represent a halogen atom; and p and q independently are an integer in the range of 0 to 3.

9. A method according to claim 1, wherein said photo-bromination reaction is carried out while removing hydrogen bromide generated in the reaction system.

10. A method according to claim 1, wherein said aromatic compound (II) is a compound represented by the following formula (2):

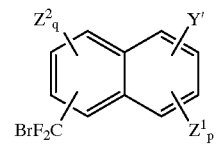
(2)

wherein Y' represent —$CF_2H$, —$CF_2Br$, or —CHO group; $Z^1$ and $Z^2$ independently represent a halogen atom; and p and q independently are an integer in the range of 0 to 3.

11. A method according to claim 10, wherein said aromatic compound (II) is a compound represented by the following formula:

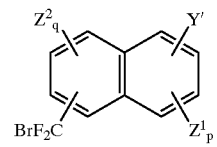

wherein Y' represents —$CF_2H$, —$CF_2Br$, or —CHO group; $Z^1$ and $Z^2$ independently represent a halogen atom; and p and q independently are an integer in the range of 0 to 3.

12. A method according to claim 11, wherein said aromatic compound (II) is a compound represented by any one of the following three formulae:

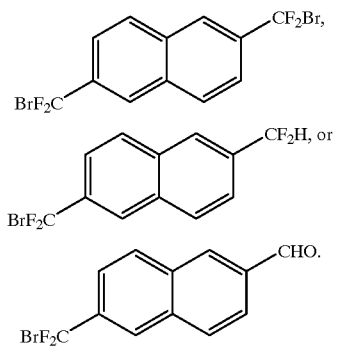

13. A halogen-containing naphthalene compound represented by the following formula (1):

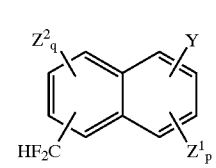
(1)

wherein Y represents —$CF_2H$, —$CF_2Br$, or —CHO group, $Z^1$ and $Z^2$ independently represent a halogen atom, and p and q independently are an integer in the range of 0 to 3.

* * * * *